US008450530B2

(12) United States Patent
Mueller et al.

(10) Patent No.: US 8,450,530 B2
(45) Date of Patent: May 28, 2013

(54) PROCESS FOR PREPARING UNSYMMETRIC SECONDARY TERT-BUTYLAMINES IN THE GAS PHASE

(75) Inventors: Christoph Mueller, Mannheim (DE); Christof Wilhelm Wigbers, Mannheim (DE); Johann-Peter Melder, Boehl-Iggelheim (DE); Gerd Haderlein, Gruenstadt (DE); Norbert Gutfrucht, Lambrecht (DE)

(73) Assignee: BASF SE, Ludwigshafen (DE)

( * ) Notice: Subject to any disclaimer, the term of this patent is extended or adjusted under 35 U.S.C. 154(b) by 118 days.

(21) Appl. No.: 13/080,885

(22) Filed: Apr. 6, 2011

(65) Prior Publication Data

US 2011/0251434 A1 Oct. 13, 2011

Related U.S. Application Data

(60) Provisional application No. 61/321,522, filed on Apr. 7, 2010.

(51) Int. Cl.
*C07C 209/16* (2006.01)
*C07C 209/26* (2006.01)

(52) U.S. Cl.
USPC ........... 564/479; 564/397; 564/398; 564/446; 564/473; 564/480

(58) Field of Classification Search
None
See application file for complete search history.

(56) References Cited

U.S. PATENT DOCUMENTS

| 6,689,914 | B2 * | 2/2004 | Schafer et al. ................. 564/480 |
| 2007/0232833 | A1 | 10/2007 | Haese et al. |
| 2011/0137029 | A1 | 6/2011 | Kubanek et al. |
| 2011/0137030 | A1 | 6/2011 | Kubanek et al. |

FOREIGN PATENT DOCUMENTS

| DE | 198 59 776 A1 | 6/2000 |
| EP | 0 233 317 A1 | 8/1987 |
| EP | 1 312 600 B1 | 8/2004 |
| EP | 1 312 599 B1 | 3/2006 |
| JP | 2011-26214 | 2/2011 |
| WO | WO 2004/009529 A1 | 1/2004 |
| WO | WO 2005/110969 A1 | 11/2005 |
| WO | WO 2009/084538 A1 | 7/2009 |

OTHER PUBLICATIONS

Prades et al., Chemistry-A European Journal (2008), 14(36), p. 11474-11479.*
International Search Report issued Jul. 19, 2011 in corresponding International Application No. PCT/EP2011/055286 (with an English Translation of Categories).
J. C. Stowell et al., "Preparation of Sterically Hindered Secondary Amines", Synthesis, No. 2, 1974, XP 002643797, pp. 127-128.
U.S. Appl. No. 13/119,948, filed Mar. 18, 2011, Ernst, et al.
U.S. Appl. No. 13/080,080, filed Apr. 5, 2011, Wigbers, et al.
Jeffrey C. Bottaro, et al., "Improved Synthesis of Cubane-1,2,4,7-tetracarboxylic Acid", Journal of Organic Chemistry, vol. 56, No. 3, 1991, pp. 1305-1307.
Martin Newcomb, et al., "Mechanism of Reduction of Trityl Halides by Lithium Dialkylamide Bases", Journal of the American Chemical Society, vol. 112, No. 13, 1990, pp. 5186-5193.
Yu. D. Smirnov, et al., "Electrochemical Reductive Amination, II. Amination of Aliphatic Aldehydes With Primary Amines", Zhurnal Organicheskoi Khimii, vol. 28, No. 3, 1992, pp. 374-380.
Silvia Gomez, et al., "The Reductive Amination of Aldehydes and Ketones and the Hydrogenation of Nitriles: Mechanistic Aspects and Selectivity Control", Advanced Synthesis & Catalysis, vol. 344, No. 10, 2002, pp. 1037-1057.
F. Müller, et al., "Houben-Weyl, Methoden der organischen Chemie [Methods of Organic Chemistry]", $4^{th}$ Edition, vol. 11/1, 1957, p. 602.
Tamas Mallat, et al., "Amination Reactions", Handbook of Heterogeneous Catalysis, Wiley VCH, $2^{nd}$ Edition, vol. 7, 2008, p. 3548.
Gerhart Eigenberger, "Fixed-Bed Reactors", Ullmann's Encyclopedia of Industrial Chemistry, $5^{th}$ Edition, vol. B. 4, 1992, pp. 199-238.
"Distillation", Kirk-Othmer, Encyclopedia of Chemical Technology, $3^{rd}$ Edition, vol. 7, 1979, pp. 870-881.
U.S. Appl. No. 13/516,479, filed Jun. 15, 2012, Maegerlein, et al.
U.S. Appl. No. 13/516,521, filed Jun. 15, 2012, Maegerlein et al.

* cited by examiner

*Primary Examiner* — Brian J Davis
(74) *Attorney, Agent, or Firm* — Oblon, Spivak, McClelland, Maier & Neustadt, L.L.P.

(57) ABSTRACT

The present invention relates to a process for preparing unsymmetric secondary tert-butylamines by continuous amination in the gas phase, wherein tert-butylamine is converted over hydrogenation catalysts in the presence of an alcohol or aldehyde and hydrogen.

12 Claims, No Drawings

PROCESS FOR PREPARING UNSYMMETRIC SECONDARY TERT-BUTYLAMINES IN THE GAS PHASE

This application claims the benefit of U.S. provisional application Ser. No. 61/321,522, filed Apr. 7, 2010.

The present invention relates to a process for preparing unsymmetric secondary tert-butylamines by continuous amination in the gas phase, wherein tert-butylamine is converted over hydrogenation catalysts in the presence of an alcohol or aldehyde and hydrogen.

Secondary amines are important, industrially utilized substances. They serve, for example, as polymerization and curing catalysts for the production of polymer moldings based on epoxides and polyurethanes, as corrosion inhibitors and as starting materials for flocculants and detergents. In addition, secondary amines are used as intermediates in crop protection.

Unsymmetric amines with tert-butyl and alkyl radicals are described as starting materials for preparation of vulcanization accelerators for rubber in WO-A 2009/084538, and are of particular interest.

Secondary amines are obtainable by alkylating primary amines with alkyl halides, by acetylation of primary amines and subsequent reduction of the carbonyl group with lithium aluminum hydride, and by reductive, especially hydrogenating, amination of aldehydes with primary amines.

This is in principle also true of unsymmetric secondary amines comprising tert-butyl groups:

J. C. Bottaro et al. state, in Journal of Organic Chemistry, 1991, 56, pages 1305 to 1307, that ethyl-tert-butylamine is preparable by reaction of tert-butylamine with ethyl bromide in a molar ratio of 3:1 with 85% yield. Disadvantages of this process are that the hydrogen bromide obtained leads to occurrence of salts after neutralization, that excess tert-butylamine has to be removed and recycled for economic reasons, and that corrosion problems occur.

M. Newcomb et al. describe, in contrast, in Journal of the American Chemical Society, 1990, 112, pages 5186 to 5193, acetylating tert-butylamine with acetic anhydride (40% yield) and reducing the resulting N-tert-butylacetamide with lithium aluminum hydride to ethyl-tert-butylamine. However, the process has two stages, enables only low yields and is afflicted by the occurrence of oxygen-containing aluminum compounds.

Yu. Smirnow et al. state, in Zhurnal Organicheskoi Khimii (1992), 28 (3), pages 461 to 467, that ethyl-tert-butylamine is also preparable by electrochemical reductive amination of acetaldehyde with tert-butylamines over lead cathodes in 60% yield. A particular disadvantage is the low yields.

The amination of alcohols with primary amines and hydrogen in the presence of hydrogenation catalysts to corresponding unsymmetric secondary amines is likewise known. For instance, EP-A 233 317 already states that secondary and tertiary amines can be prepared by reaction of primary or secondary alcohols which comprise 1 to 5 carbon atoms with primary or secondary amines in the gas phase in the presence of hydrogen and catalysts comprising copper and chromium oxides (42% by weight of CuO, 38% by weight of $Cr_2O_3$, 20% by weight of $Al_2O_3$). A process for preparing unsymmetric tert-butylamines in high yields is not described. The sole working example for the synthesis of secondary amines is the reaction of n-butanol with ethylamine in a molar ratio of 3:1 at 174-180° C. to give N-ethyl-n-butylamine. The n-butanol conversion is 52.9%, the N-ethyl-n-butyl selectivity 81.6%. Another disadvantage is the high distillation expenditure for the workup of the hydrogenation output which consists of unconverted n-butanol to an extent of 69.2% by weight, of unconverted ethylamine to an extent of 8.1% by weight and of the N-ethyl-n-butylamine target product only to an extent of 16.7% by weight. A further disadvantage consists in the use of catalysts which are problematic with regard to environmental pollution owing to the chromium content thereof.

DE-A 198 59 776 states that the amination is performed in the gas phase at temperatures of 80 to 300° C., preferably at 120 to 270° C., more preferably at 160 to 250° C. The pressures are 1 to 400 bar, preferably 1 to 100 bar, more preferably from 1 to 50 bar. The catalyst hourly space velocity is in the range from 0.01 to 2 kg and preferably 0.05 to 0.5 kg of alcohol per liter of catalyst (bed volume) and hour. Stoichiometric, substoichiometric or superstoichiometric amounts of primary or secondary amines, preferably approximately stoichiometric amounts, are employed per mole of alcohol or aldehyde. The catalysts used are copper and oxygen compounds of titanium in the form of shaped bodies, which are produced with addition of metallic copper. Although tert-butylamine is included in the general formula III of DE-A 198 59 776, being a preferred aminating agent it is explicitly omitted in the series of the $C_4$-alkylamines.

WO-A 2005/110969 discloses that alcohols, but especially aldehydes, can be reacted in the gas phase with primary or secondary amines in the presence of hydrogen and copper-comprising catalysts isothermally to give secondary or tertiary amines. The amination is performed at 80 to 300° C., preferably 150 to 250° C., more preferably 170 to 230° C., and absolute pressures of 1 to 300 bar, preferably 1 to 50 bar, more preferably 1 to 30 bar. The catalyst hourly space velocity is in the range from 0.1 to 2.0 kg, preferably 0.1 to 1.0 kg and more preferably 0.2 to 0.6 kg of alcohol per liter of catalyst and hour. Before being reduced with hydrogen, the catalytically active material of the catalyst precursor comprises aluminum oxide, zirconium dioxide, titanium dioxide and/or silicon dioxide. The amine component is preferably used in 0.9 to 100 times the molar amount, especially 1 to 10 times the molar amount, based in each case on the alcohol or aldehyde used. Working examples for preparation of secondary amines I proceeding from alcohols or aldehydes and tert-butylamine are not included in the twelve examples.

Advanced Synthesis & Catalysis, 2002, 344, page 1041, chapter 3.1, first paragraph, states that, in the reaction of an amine with a carbonyl compound, yields and selectivities depend to a high degree on the steric hindrance of the starting compounds. According to Advanced Synthesis & Catalysis, this steric hindrance also plays a role in the region of the amine function (chapter 3.1, third paragraph). For instance, in the reductive amination of acetone with 2,4,6-trimethylaniline, the secondary amine forms only in 36% yield, but with aniline with 98% yield (chapter 3.1, third paragraph and scheme 10). The person skilled in the art can thus infer the teaching from Advanced Synthesis & Catalysis that low yields and selectivities for the unsymmetric secondary tert-butylamine of the formula I have to be expected in the amination of alcohols or aldehydes with tert-butylamine.

It is therefore an object of the present invention to provide a continuous process for aminating alcohols or aldehydes with tert-butylamine and hydrogen in the presence of hydrogenation catalysts, which enables the unsymmetric secondary tert-butylamines of the formula I, which intrinsically have high steric hindrance, to be obtained with good yields and high selectivity without using environmentally polluting catalysts.

It is a further object of the process to ensure a simple and productive workup of the process product.

This object is achieved by a process for preparing unsymmetric secondary tert-butylamines of the formula I $$R-CH_2-NH-\underset{\underset{CH_3}{|}}{\overset{\overset{CH_3}{|}}{C}}-CH_3 \quad \text{I}$$

where R is selected from the group of hydrogen, linear or branched aliphatic radicals having one to 15 carbon atoms, cycloaliphatic radicals having 5 to 10 carbon atoms, aralkyl radicals or phenyl radicals which may be o-, m- and/or p-substituted by aliphatic radicals having one to 4 carbon atoms, by continuously aminating alcohols of the formula II or aldehydes of the formula III with tert-butylamine and hydrogen in the gas phase in the presence of hydrogenation catalysts, comprising the following steps:
(i) providing a reactor filled with the hydrogenation catalyst,
(ii) heating the reactor to temperatures in the range from 60 to 240° C. and applying a pressure in the range from 1 to 100 bar,
(iii) continuously adding hydrogen, tert-butylamine and an alcohol of the formula II $$R-CH_2OH \quad \text{II}$$

or an aldehyde of the formula III $$R-CHO \quad \text{III}$$

to the reactor according to step (ii), where the molar ratio of alcohol of the formula II or aldehyde of the formula III to tert-butylamine is in the range from 0.5:1 to 1.4:1, and R both for the alcohol of the formula II and for the aldehyde of the formula III is as defined for R in formula I,
(iv) cooling and decompressing the reactor and withdrawing the hydrogenation output obtained from step (iii).

The inventive reaction with an alcohol of the formula II can be described by the following formula equation:

$$R-CH_2-OH + H_2N-\underset{\underset{CH_3}{|}}{\overset{\overset{CH_3}{|}}{C}}-CH_3 \xrightarrow{[cat]}$$
$$R-CH_2-HN-\underset{\underset{CH_3}{|}}{\overset{\overset{CH_3}{|}}{C}}-CH_3 + H_2O$$

The amination is performed continuously in the gas phase. tert-Butylamine with a boiling point of 44° C. at 1013 mbar, an alcohol of the formula II $$R-CH_2-OH \quad \text{II}$$

or an aldehyde of the formula III $$R-CHO \quad \text{III}$$

and optionally solvent are supplied to the hydrogenation reactor in gaseous form, where R both in the unsymmetric secondary tert-butylamine of the formula I and the alcohol of the formula II and the aldehyde of the formula III is selected from the group of hydrogen, linear or branched aliphatic radicals having one to 15 carbon atoms, cycloaliphatic radicals having 5 to 10 carbon atoms, aralkyl radicals or phenyl radicals which may be o-, m- and/or p-substituted by aliphatic radicals having one to 4 carbon atoms. The aralkyl or phenyl radicals are preferably substituted by aliphatic radicals selected from the group of methyl, ethyl n-propyl, i-propyl, n-butyl, i-butyl, sec-butyl and/or tert-butyl groups.

Preferred primary alcohols of the formula II are selected from the group of methanol, ethanol, n-propanol, n-butanol, 2-methyl-1-propanol, pivalyl alcohol, n-pentanol, n-hexanol, 2-ethylhexanol, 2-methyl-1-pentanol, 3-methyl-1-pentanol, 4-methyl-1-pentanol, n-octanol, n-decanol, n-undecanol, n-dodecanol, 2-phenylethanol, 2-cyclopentylethanol, 2-cyclohexylethanol, 2-cycloheptylethanol, methylphenylethanol, benzyl alcohol, methylbenzyl alcohol or mixtures of these alcohols suitable.

Particularly preferred primary alcohols of the formula II are selected from the group of methanol, ethanol, n-propanol, n-butanol, 2-methyl-1-propanol, n-pentanol and mixtures of these compounds.

Very particular preference is given to primary alcohols of the formula II selected from the group of methanol, ethanol, n-propanol, n-butanol, 2-methyl-1-propanol or mixtures of these alcohols. The primary alcohol of the formula II is very essentially preferably ethanol or n-butanol.

Instead of the primary alcohols II, it is also possible to use the aldehydes III formed by dehydrogenation of the alcohols II as starting compounds in the gas phase, in which case at least 1 equivalent of hydrogen must be present during the hydrogenation in the reactor.

Preference is given, however, to the use of primary alcohols of the formula II. The amination of the process according to the invention is performed at temperatures in the range from 60 to 240° C., preferably in the range from 80 to 230° C. The alcohols of the formula II are aminated at temperatures of 150 to 240° C., preferably 170 to 230° C., more preferably 180 to 220° C. When the amination is performed with the aldehydes of the formula III as starting compounds, temperatures of 60 to 200° C., preferably 80 to 170° C., more preferably 100 to 150° C., are maintained.

According to the stoichiometry of the amination, proceeding from alcohols, no hydrogen is required. However, it is advisable to supply hydrogen, preferably in an amount of 150 to 250 l (STP), more preferably in amounts of 180 to 220 l (STP), of hydrogen per liter of catalyst and hour. In the case of use of aldehydes of the formula III, at least one mole of hydrogen must be present per mole of aldehyde III.

The total pressure in the reactor at the particular temperature is thus composed of the partial pressures of the feedstocks and of the reaction products, i.e. hydrogen, tert-butylamine, alcohol of the formula II or aldehyde of the formula III, unsymmetric secondary tert-butylamine I, water and any additional solvent used. Injecting hydrogen increases the pressure to the desired reaction pressure. In order to compensate for the consumption of hydrogen, the total pressure is kept constant over the entire reaction time by injecting further hydrogen.

The total pressure is 1 to 100 bar, preferably 1 to 50 bar, more preferably 1 to 25 bar, especially preferably 1 to 20 bar.

The molar ratio of alcohol of the formula II or aldehyde of the formula III to tert-butylamine is preferably in the range from 1.4:1 to 0.5:1, more preferably in the range from 1.0:1 to 0.5:1, most preferably in the range from 0.8:1 to 0.5:1. The selection of these molar ratios achieves a high conversion of the alcohols of the formula II or of the aldehydes of the formula III. At the same time, the selection of these molar ratios results in a high selectivity for the secondary amine of the formula I.

It may be advantageous to perform the process according to the invention in the presence of a solvent which is inert under the reaction conditions. These inert solvents are selected from the group of N-methylpyrrolidone or ethers such as tetrahydrofuran, dioxane, ethylene glycol dimethyl ether.

Preference is given, however, to working in the absence of a solvent.

The catalyst hourly space velocity is generally in the range from 0.05 to 0.5 kg, preferably 0.1 to 0.4 kg, and more preferably 0.2 to 0.3 kg of alcohol of the formula II or aldehyde of the formula III per liter of catalyst (bed volume) and hour.

The catalysts used for the process according to the invention may be all hydrogenation catalysts known to those skilled in the art, as described, for example, in Houben-Weyl, Methoden der organischen Chemie [Methods of Organic Chemistry], 4th edition, volume 11/1, page 602, and Handbook of heterogeneous catalysis, 2nd edition, volume 7, page 3548, Wiley VCH. Accordingly, useful catalysts are the metals and/or the oxygen compounds of the metals nickel, cobalt, ruthenium, rhodium, palladium, platinum and copper, or mixtures of these metals and/or of the oxygen compounds of these metals. Cobalt, copper and nickel are also suitable as Raney catalysts.

For the process according to the invention using alcohols of the formula II, preference is given to catalysts comprising copper oxides, the copper oxide having been applied to oxidic supports. The amount of copper oxide, calculated as CuO, is 1 to 70% by weight, preferably 2 to 65% by weight, more preferably 3 to 60% by weight, based on the total mass of the oxidic catalyst precursor. This catalyst precursor is hydrogenated to elemental copper either before the hydrogenation or in the initial phase of the hydrogenation in the presence of alcohols II or aldehydes III. Suitable catalyst supports are, for example, aluminum oxide, silicon dioxide, titanium dioxide, zirconium dioxide and/or activated carbon. In this context, catalytically active material is understood to mean the sum of oxygen-comprising copper compounds and oxidic supports. Particular preference is given to a catalyst precursor which consists of copper oxide to an extent of 1 to 70% by weight and the remainder to 100% consists of aluminum oxide.

The catalytically active material of the catalysts used in the process according to the invention may further comprise one or more elements of oxidation state 0 or the inorganic or organic compounds thereof, selected from groups I A to VI A and I B to VII B and VIII of the Periodic Table of the Elements.

The preparation of supported copper catalysts is described in detail in applications WO 2005/110969 and DE 19859776. The content of these applications is fully incorporated into the present application.

Preferably, a catalyst hourly space velocity within a range from 0.1 to 0.3 kg of tert-butylamine per l of catalyst per hour is established for the process according to the invention. Within this range, both the selectivity for the secondary amine of the formula I and the conversion of the tert-butylamine used are favorable. At higher catalyst hourly space velocities the conversion of the tert-butylamine used is low, and at lower catalyst hourly space velocities by-product (tertiary amine of the formula IV) is formed to an enhanced degree, which reduces the selectivity for the product (secondary amine of the formula I). More preferably, a catalyst hourly space velocity of 0.15 to 0.25 kg of tert-butylamine per l of catalyst per hour is established. These catalyst hourly space velocities are more preferably established in combination with the use of a CuO-containing catalyst, especially with one whose catalyst precursor consists to an extent of 1 to 70% by weight of copper oxide and, in the proportion remaining to 100%, of aluminum oxide.

Preferred reactors are tubular reactors, the process according to the invention preferably being performed in circulation mode. Circulation mode is understood to mean that unconverted hydrogen is not discharged from the process but is recycled into the hydrogenation reactor together with compounds which are gaseous under the reaction conditions of the hydrogenation output condensation.

The oxidic catalyst precursors are ground, mixed with shaping assistants, shaped to tablets, spheres, rings or extrudates, and reduced with hydrogen either outside or within the reactor, and arranged in a fixed manner in the reactor.

The reactants are evaporated and passed continuously in liquid phase or trickle mode over catalyst present in the reactor.

It is also possible to perform the process according to the invention in a fluidized bed with catalyst material in upward and downward motion.

The gas stream obtained in the condensation of the gaseous reaction output, which comprises excess hydrogen and possibly starting compounds, is recycled into the hydrogenation (cycle gas). In a preferred embodiment, the cycle gas can be used to evaporate the reactants and simultaneously also comprises the hydrogen reactant for the process according to the invention.

The cycle gas comprises preferably at least 10%, more preferably 50 to 100% and most preferably 80 to 100% by volume of hydrogen.

The cycle gas rate at operating pressure is preferably in the range from 40 to 1000 m$^3$ per m$^3$ of catalyst and hour, especially from 100 to 700 m$^3$ per m$^3$ of catalyst and hour. The starting materials are supplied in gaseous form to the reactor after evaporation in the cycle gas. However, it is also possible to evaporate the reactants and to mix them into the cycle gas in gaseous form.

The offgas rate discharged from the cycle stream is within a range from 5 to 800 standard cubic meters per hour, especially 20 to 300 standard cubic meters per hour.

Suitable reactors for a cycle gas method are described in Ullmanns Encyclopedia of Industrial Chemistry, 5th edition, volume B 4, pages 199-238, "Fixed-Bed Reactors". FIG. 2 in DE 198 59 776 shows a continuously operable gas phase pressure apparatus in which the reactants are conducted into the cycle gas.

Very particular preference is given to performing the amination in a tube bundle reactor or in a single-stream plant. In a single-stream plant, the tubular reactor consists of a series connection of a plurality of, for example two or three, individual tubular reactors.

It is advantageous for the process according to the invention when the hydrogenation output after step (iv) of the process according to the invention is worked up appropriately. In addition to the target product, the unsymmetric secondary tert-butylamine of the formula I, the liquid hydrogenation output obtained after cooling and decompression comprises, as by-products, small amounts of tertiary tert-butylamines of the formula IV

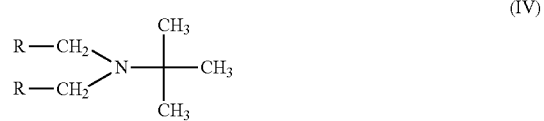

(IV)

and also excess tert-butylamine and possibly small amounts of alcohols of the formula II. Small amounts are understood in each case to mean less than 5% by weight, preferably less than 3% by weight and more preferably less than 1% by weight of the compounds specified in each case.

The amination forms about 5 to 20% by weight of water, based on the amount of the catalyst-free hydrogenation output. The unsymmetric secondary tert-butylamines of the formula I form azeotropes with water. It is therefore possible to remove only mixtures which comprise water of reaction and the amine I by distillation from the hydrogenation output.

EP-B 1312599 and EP-B 1312600 describe the separation of amine-containing mixtures which comprise one or more amines, water, low boilers and high boilers. The separation is effected by
(i) the distillative removal of low boilers from the amine-containing mixture,
(ii) optional distillative removal of high boilers from the amine-containing mixture,
(iii) extraction of the amine-containing mixture with sodium hydroxide solution to obtain in an aqueous first phase comprising sodium hydroxide solution, and an aqueous-organic second phase comprising amine,
(iv) distillation of the aqueous-organic second phase to obtain amine/water azeotrope and essentially anhydrous amine, and recycling of the amine/water azeotrope into the extraction step (iii).

The essentially anhydrous amine has to be purified further by distillation. In one working example, the component steps of the workup are demonstrated using a hydrogenation output which was obtained by reductive amination of 1,5-pentanediol with ammonia to form piperidine.

For the process according to the invention, preference is likewise given to a workup of the hydrogenation output which comprises both a distillation and the breaking of an amine/water azeotrope with an aqueous alkali metal hydroxide and/or alkaline earth metal hydroxide solution. Both the distillation and the breaking of the amine/water azeotrope can be performed batchwise or continuously.

In contrast to the prior art, for the process according to the invention, a first step is the breaking of the unsymmetric secondary tert-butylamine of the formula I/water azeotrope by treatment of the hydrogenation output with aqueous alkali metal hydroxide and/or alkaline earth metal hydroxide solution. The alkali metal hydroxide and/or alkaline earth metal hydroxide concentration in the aqueous solution may be 1 to 75% by weight, preferably 25 to 50% by weight. Preferred aqueous alkali metal hydroxide and/or alkaline earth metal hydroxide solutions are selected from the group of sodium hydroxide solution, potassium hydroxide solution, magnesium hydroxide, calcium hydroxide. Preference is given to sodium hydroxide solution. Particular preference is given to 50% by weight sodium hydroxide solution.

After extraction of the hydrogenation output with the aqueous alkali metal hydroxide and/or alkaline earth metal hydroxide solution, it is removed by phase separation. The residual water content of the organic phase can be determined, for example, by Karl Fischer titration. The amount of alkali metal hydroxide and/or alkaline earth metal hydroxide solution required for the water removal can be determined by a few preliminary tests.

The extraction apparatus used for the extraction with alkali metal hydroxide and/or alkaline earth metal hydroxide solution may have a one-stage or multistage configuration, for example a single mixer-settler extractor. Multistage extractions are, for example, extraction columns or extraction cascades. Suitable extraction columns are, for example, columns with random packing, sieve tray columns, cascade columns, pulsed columns, rotary columns and centrifugal columns. An extraction cascade is, for example, a plurality of mixer-settler extractors connected in series, which may also be configured in a space-saving manner as a tower extractor or box extractor. When the extractor is a multistage extractor, preferably a countercurrent extraction column with generally 1 to 25 and preferably 4 to 10 theoretical plates is preferred. The latter is generally operated at a pressure at which all components of the extraction mixture are below their boiling points, and a viscosity of the two phases at which dispersion of the two phases is possible without any problem is additionally established. The temperature is generally 5 to 200° C., preferably 20 to 70° C., more preferably 40 to 50° C. After phase separation, the aqueous phase comprising alkali metal hydroxide and/or alkaline earth metal hydroxide solution is discharged from the process.

If the aqueous alkali metal hydroxide and/or alkaline earth metal hydroxide solution removed comprises significant amounts of unsymmetric secondary tert-butylamine of the formula I, alcohol of the formula II and/or aldehyde of the formula III and/or tert-butylamine, these compounds can be recovered by extraction with organic solvents. Significant amounts are present when the sum of the above compounds is more than 10% by weight, preferably more than 5% by weight, more preferably more than 2% by weight, based on the anhydrous and catalyst-free hydrogenation output.

Useful organic solvents include, for example, aliphatic, cycloaliphatic or aromatic hydrocarbons which possess a miscibility gap with aqueous alkali metal hydroxide and/or alkaline earth metal hydroxide solution. Examples of such hydrocarbons are n-hexane, n-octane, cyclohexane, toluene and ethylbenzene, or mixtures of these compounds.

The aqueous alkali metal hydroxide and/or alkaline earth metal hydroxide solution phase is removed from the hydrocarbon phase by phase separation. The hydrocarbon is removed from the hydrocarbon phase by distillation. The unsymmetric secondary tert-butylamine of the formula I, alcohol of the formula II and/or aldehyde of the formula III and/or tert-butylamine recovered can be combined with the majority of crude unsymmetric secondary tert-butylamine of the formula I, which has been obtained from the first organic phase by extraction after phase separation, and purified by distillation.

It is additionally possible to break the azeotrope of unsymmetric secondary tert-butylamine of the formula I and water by adding hydrocarbons to the hydrogenation output, distilling hydrocarbon/water heteroazeotropes out of the hydrogenation output, removing the water phase from the hydrocarbon phase and recycling the hydrocarbon phase into the distillation.

A further option is first to distillatively remove the azeotrope composed of unsymmetric secondary tert-butylamine of the formula I and water and only then to perform the dewatering by treatment with sodium hydroxide solution or distillation with hydrocarbons.

Finally, the removal of water by treatment with alkali metal hydroxide and/or alkaline earth metal hydroxide solution can be combined with the removal of water by distillation with hydrocarbons. In this case, the majority of water in the hydrogenation output is removed by treatment with alkali metal hydroxide and/or alkaline earth metal hydroxide solution, for example by one-stage extraction with alkali metal hydroxide and/or alkaline earth metal hydroxide solution, the phases are separated, the hydrocarbon phase removed is combined with the catalyst-free hydrogenation output, and the water still present, or a portion thereof, is removed by azeotropic distillation.

In a particularly preferred process, the water is not removed completely before the distillative workup of the hydrogenation output. It is preferred when the water content of the hydrogenation output is less than 5% by weight, preferably less than 3% by weight, more preferably less than 0.9% by weight. When only a small amount of residual water is present, only a little unsymmetric secondary tert-butylamine of the formula I is discharged as an azeotrope with water in the distillation. Small amounts of azeotrope, for example those which comprise less than one mol % of unsymmetric secondary tert-butylamine of the formula I, based on tert-butylamine used, can optionally be discarded. However, it is also possible to recycle the azeotrope into the extraction with alkali metal hydroxide and/or alkaline earth metal hydroxide solution. It is advantageous to need only a one-stage treatment of the hydrogenation output with alkali metal hydroxide and/or alkaline earth metal hydroxide solution. No fine adjustment of the amount of alkali metal hydroxide and/or alkaline earth metal hydroxide solution is necessary in order also to remove the last residues of water.

The hydrogenation output which is anhydrous or comprises only less than 5%, preferably less than 3% and more preferably less than 1% by weight of water can be purified further by fractional distillation. Depending on the amounts to be distilled, the distillation can be performed continuously or batchwise. In this distillation, if present, unconverted tert-butylamine, unconverted alcohol of the formula II and alcohols formed from the aldehydes of the formula III distill overhead in first mixed fractions. They are then followed by the unsymmetric secondary tert-butylamine of the formula I, which is likewise distilled off overhead. In the bottoms remain, if present, tertiary amines of the formula IV and high boilers. Fractions comprising less than 97 area %, more preferably less than 98 area % and more preferably less than 99 area % of secondary amine by GC analysis can be recycled into the distillation.

For the fractional distillation, customary apparatus is useful, as described, for example, in Kirk-Othmer, Encyclopedia of Chemical Technology, 3. Edition, Volume 7, John Wiley and Sons, New York, 1979, pages 870 to 881. Preference is given to sieve tray columns, bubble-cap tray columns, columns with structure packing or columns with random packing.

Fractional distillation achieves purities of the unsymmetric secondary tert-butylamines of the formula I of more than 98 area %, especially more than 99 area %, more preferably of more than 99.5 area %, especially more than 99.9 (GC analysis).

For the continuous workup according to the disclosure of EP-B 1312599 and EP-B 1312600, FIGS. 1 and 2, three to four tailored distillation columns and one extraction apparatus are required.

In the inventive batchwise workup, in contrast, only one distillation column and one extraction apparatus are used.

EXAMPLES

Example 1

Amination of Ethanol with Tert-Butylamine in the Gas Phase

The experiment was carried out in an oil-heated glass reactor (length 1 m, diameter 40 mm) at ambient pressure. The reactor was operated in trickle mode. The lower part of the reactor was filled with 300 ml of V2A mesh rings (diameter 5 mm), and above those 200 ml (180 g) of copper catalyst which has been reduced with hydrogen at 180 to 200° C. and then passivated with oxygen (3×3 mm tablets). Before the reduction and passivation, the copper catalyst consisted of copper oxide (CuO) to an extent of 55% by weight and of aluminum oxide to an extent of 45% by weight. The upper part of the reactor was charged with 500 ml of V2A mesh rings. The reactor was heated by an oil circuit. Hydrogen and mixtures of tert-butylamine and alcohol of the formula II were pumped continuously into the reactor. The hydrogenation output was cooled, decompressed and analyzed by gas chromatography (DB 1 column, temperature program 60-280° C., 10° C. per minute). The selectivity and conversion figures are based on GC area percent.

In example 1, 40 g of tert-butylamine (0.55 mol), 20 g of ethanol (0.44 mol) and 40 l (STP) of hydrogen per hour were conducted over the copper catalyst at 210° C. The molar ratio of tert-butylamine to alcohol was 1:0.8, the catalyst hourly space velocity 0.2 kg of tert-butylamine per liter of catalyst and hour.

In table 1, the reaction conditions and the results of the gas chromatography analysis are compiled.

Inventive example 1 shows that the selectivity for the ethyl-tert-butylamine target product is 97%, that for the diethyl-tert-butylamine by-product 1%, and the tert-butylamine conversion 75%.

Example 2 a) Amination of Ethanol with Tert-Butylamine in the Gas Phase

The amination was performed in a tubular reactor (length 3.5 m, internal diameter 40 mm) at 220° C. and total pressure 20 bar. The reactor was operated in trickle mode. It comprised 1000 ml (900 g) of a fresh charge of the copper catalyst (H3-82, 3×3 mm tablets) which had been reduced with hydrogen at 180 to 200° C. and then passivated with oxygen, and was used in example 1.

300 g of tert-butylamine (4.1 mol), 96 g of ethanol (2.05 mol) and 300 l (STP) of hydrogen per hour were passed in gaseous form over the copper catalyst in trickle mode. The cycle gas rate was 3.2 m$^3$ (STP)/h. The molar ratio of tert-butylamine to ethanol was 1:0.5, the catalyst hourly space velocity 0.3 kg of tert-butylamine per liter of catalyst and hour.

In table 1, example 2, the reaction conditions and the results of the gas chromatography analysis are compiled.

Inventive example 2 shows that the selectivity for the ethyl-tert-butylamine target product is 99%, that for the diethyl-tert-butylamine by-product 1% and the tert-butylamine conversion 59%.

b) Dewatering of the Hydrogenation Output

The hydrogenation output comprised 12% by weight of water. It was stirred with 50% aqueous sodium hydroxide solution (hydrogenation output: sodium hydroxide solution volume ratio=1:1) at room temperature for one hour. Then the phases were separated. The water content of the organic phase was 0.9% by weight.

c) Distillative Workup of the Hydrogenation Output 2811 g of hydrogenation output from hydrogenation a), the water content of which had been reduced to 0.9% by weight by dewatering according to b) was worked up by distillation. A 6 l distillation still with attached column with structured packing was used (2×1.2 m column, diameter 43 mm, packing: Montz A 3-1000). The number of theoretical plates was 30, the reflux ratio 10:1. The distillation was effected batchwise at a pressure of 950 mbar. The bottom temperature rose from 77° C. to 151° C. in the course of the distillation. In the distillation, 2612 g of distillate (92.9% by weight), 150 g of distillation residue (5.3% by weight) and 9 g of cold trap content (0.3% by weight), based on the amount of hydrogenation output used in the distillation, were obtained. Fraction 1 (288 g) consisted of tert-butylamine to an extent of 99.7 area %. It can be recycled into the hydrogenation a). Fractions 2 to 7 (809 g) constituted mixtures of predominantly ethyl-tert-butylamine, and also ethanol and water. These fractions can be recycled into the distillation c), optionally after preceding dewatering in b). Fractions 8 to 15 (1515 g) consisted of ethyl-tert-butylamine to an extent of 99.1 to 99.9 area %. 82% of these fractions possessed a purity of >99.8 area %.

The distillation residue consisted of ethyl-tert-butylamine to an extent of 42% and of diethyl-tert-butylamine to an extent of 35%.

The distillative workup of example 2c) shows the advantages which arise in the hydrogenation a) from an excess of tert-butylamine relative to the alcohol: excess tert-butylamine can be removed without any problem as the top product from the rest of the hydrogenation output and recycled into the hydrogenation. Moreover, example 2c) demonstrates that tertiary tert-butylamine IV can be removed quantitatively from the secondary tert-butylamine I, and that purities of the secondary amine I of 99.8 area % or more are achievable.

Comparative Example 1

Example 1 was repeated, with the alteration that the molar ratio of tert-butylamine to ethanol was 1:2.5. Table 1 shows that the selectivity for the ethyl-tert-butylamine target product falls to 90% and the selectivity for the diethyl-tert-butylamine by-product rises to 7%. The tert-butylamine conversion was 98%.

Example 3

Example 1 was repeated, with the alteration that, instead of the Cu catalyst, a Cu/Ni catalyst (3×3 mm tablets; prepared from precatalyst with 46% CuO, 11% NiO, 44% Al$_2$O$_3$) was used for the hydrogenation. Table 1 shows a selectivity for the ethyl-tert-butylamine target product of 95% with a selectivity for the diethyl-tert-butylamine by-product of 3%. The tert-butylamine conversion was 75%.

Example 4

Example 1 was repeated, with the alteration that a catalyst hourly space velocity of only 0.1 kg of tert-butylamine per liter of catalyst and hour was established. For this purpose, 20 g of tert-butylamine (0.275 mol), 10 g of ethanol (0.22 mol) and 20 l (STP) of hydrogen per hour were conducted over the copper catalyst. Table 1 shows a selectivity for the ethyl-tert-butylamine target product of 96% with a selectivity for the diethyl-tert-butylamine by-product of 3%. The tert-butylamine conversion was 79%.

Example 5

Example 1 was repeated, with the alteration that the catalytic hydrogenation was performed at 170° C. instead of 210° C. Table 1 shows a selectivity for the ethyl-tert-butylamine target product of 94% with a selectivity for the diethyl-tert-butylamine by-product of 0%. The tert-butylamine conversion was 40%.

Example 6

Example 1 was repeated, with the alteration that the molar ratio of tert-butylamine to ethanol was 1 to 1. Table 1 shows a selectivity for the ethyl-tert-butylamine target product of 95% with a selectivity for the diethyl-tert-butylamine by-product of 2%. The tert-butylamine conversion was 82%.

Example 7

Example 1 was repeated, with the alteration that n-butanol was aminated with tert-butylamine instead of ethanol. Table 1 shows a selectivity for the n-butyl-tert-butylamine target product of 97% with a selectivity for the di-n-butyl-tert-butylamine by-product of 0%. The tert-butylamine conversion was 82%.

TABLE 1

| Example | Alcohol II used | Hydrogenation temperature [° C.] | Molar ratio of tert-butylamine to alcohol II | Catalyst hourly space velocity [kg/l cat • h] | tert-Butylamine conversion [%] | Selectivity for sec. amine I [%] | Selectivity for tert-amine IV |
|---|---|---|---|---|---|---|---|
| 1 | ethanol | 210 | 1:0.8 | 0.2 | 75 | 97 | 1 |
| 2 | ethanol | 220 | 1:0.5 | 0.3 | 59 | 99 | 1 |
| Comparative example 1 | ethanol | 210 | 1:2.5 | 0.2 | 98 | 90 | 7 |
| 3[1)] | ethanol | 210 | 1:0.8 | 0.2 | 75 | 95 | 3 |
| 4 | ethanol | 210 | 1:0.8 | 0.1 | 79 | 96 | 3 |
| 5 | ethanol | 170 | 1:0.8 | 0.2 | 40 | 94 | 0 |
| 6 | ethanol | 210 | 1:1 | 0.2 | 82 | 95 | 2 |
| 7 | n-butanol | 210 | 1:0.8 | 0.2 | 82 | 97[2)] | 0 |

[1)] catalyst: Cu/Ni
[2)] tert-butylbutylamine

The invention claimed is:

1. A process for preparing unsymmetric secondary tert-butylamines of the formula I

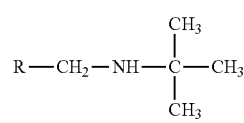

where R is selected from the group of hydrogen, linear or branched aliphatic radicals having one to 15 carbon atoms, cycloaliphatic radicals having 5 to 10 carbon atoms, aralkyl radicals or phenyl radicals which may be o-, m- and/or p-substituted by aliphatic radicals having one to 4 carbon atoms, by continuously aminating alcohols of the formula II or aldehydes of the formula III with tert-butylamine and hydrogen in the gas phase in the presence of hydrogenation catalysts, comprising the following steps:
(i) providing a reactor filled with the hydrogenation catalyst,
(ii) heating the reactor to temperatures in the range from 60 to 240° C. and applying a pressure in the range from 1 to 100 bar,
(iii) continuously adding hydrogen, tert-butylamine and an alcohol of the formula II

    II or an aldehyde of the formula III

    III to the reactor according to step (ii), where the molar ratio of alcohol of the formula II or aldehyde of the formula III to tert-butylamine is in the range from 0.5:1 to 1.4:1, and R both for the alcohol of the formula II and for the aldehyde of the formula III is as defined for R in formula I,
(iv) cooling and decompressing the reactor and withdrawing the hydrogenation output obtained from step (iii).

2. The process according to claim 1, wherein the hydrogenation output according to step (iv) is subjected to the following workup steps:
a) extracting the hydrogenation output from step (iv) with an aqueous alkali metal hydroxide and/or alkaline earth metal hydroxide solution resulting in an aqueous phase and an organic phase,
b) removing the aqueous phase obtained from step a) from the organic phase and
c) fractionally distilling the organic phase obtained from step b).

3. The process according to claim 2, wherein
α) the aqueous phase obtained from step b) is admixed with at least of an aliphatic hydrocarbon, a cycloaliphatic hydrocarbon, an aromatic hydrocarbon which have a miscibility gap with aqueous alkali metal hydroxide and/or alkaline earth metal hydroxide solution when the content of the sum of the compounds of the formula I, of the alcohol of the formula II or of the aldehyde of the formula III and tert-butylamine is more than 2% by weight of the hydrogenation output from step (iv),
β) the hydrocarbon phase is subsequently removed from the aqueous phase,
γ) the hydrocarbon is distillatively removed from the hydrocarbon phase
δ) and the residue of the distillation is combined with the organic phase obtained from step b).

4. The process according to claim 2, wherein the water content of the organic phase obtained from step b) is up to 5% by weight based on the total weight of the organic phase obtained after step b).

5. The process according to claim 1, wherein R in the formula I, II and III is methyl.

6. The process according to claim 2, wherein the alkali metal hydroxide and/or alkaline earth metal hydroxide solution for the extraction according to step a) is a 1 to 75% by weight sodium hydroxide solution.

7. The process according to claim 1, wherein the hydrogenation catalyst used in step i) comprises metals and/or oxygen compounds of the metals selected from the group of nickel, cobalt, ruthenium, rhodium, palladium, platinum and copper, or mixtures of these metals.

8. The process according to claim 7, wherein the hydrogenation catalyst comprises an oxidic catalyst precursor that comprises 1 to 70% by weight of copper oxide and the remainder aluminum oxide to 100% by weight.

9. The process according to claim 1, wherein an alcohol of the formula II is used.

10. The process according to claim 1, wherein the amount of hydrogen supplied is in the range from 150 to 250 l (STP) of hydrogen per liter of catalyst and hour.

11. The process according to claim 1, which is operated in the absence of a solvent.

12. The process according to claim 1, wherein a catalyst hourly space velocity of 0.1 to 0.3 kg of tert-butylamine per 1 of hydrogenation catalyst per hour is established for the catalytic hydrogenation.

* * * * *